US006287276B1

(12) United States Patent
Feldman

(10) Patent No.: US 6,287,276 B1
(45) Date of Patent: *Sep. 11, 2001

(54) SET DEPTH NAIL NOTCHER AND METHOD FOR TREATING NAIL FUNGUS

(75) Inventor: Leonard Feldman, Brooklyn, NY (US)

(73) Assignee: Profoot, Inc., Brooklyn, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/129,680

(22) Filed: Aug. 6, 1998

(51) Int. Cl.$^7$ .......................... A61B 17/20; A61M 37/00
(52) U.S. Cl. .......................... 604/46; 604/293; 606/172; 132/75.4
(58) Field of Search .......................... 604/46, 47, 289, 604/290, 293, 500; 606/167, 170, 172, 171, 174, 176, 177; 433/25–26, 30–31, 34, 46; D24/176; 132/76.4, 76.5, 753, 754

(56) References Cited

U.S. PATENT DOCUMENTS

| D. 35,746 | 2/1902 | Clark . |
| D. 58,210 | 6/1921 | Beauregard . |
| 678,643 | 7/1901 | Clarke . |
| 833,675 | 10/1906 | Chezem . |
| 904,779 | * 11/1908 | Higgins . |
| 1,743,010 | 1/1930 | Wilmot . |
| 2,439,922 | 4/1948 | Chappell et al. . |
| 2,566,688 | 9/1951 | West . |
| 2,573,310 | 10/1951 | Collier . |
| 3,034,507 | * 5/1962 | McConnell et al. . |
| 3,600,803 | * 8/1971 | Nachsi . |
| 4,180,058 | * 12/1979 | Brem . |
| 5,391,367 | 2/1995 | DeVincentis et al. . |
| 5,422,366 | 6/1995 | Mintzis et al. . |
| 5,437,679 | * 8/1995 | Gaillard . |
| 5,464,610 | * 11/1995 | Hayes, Jr. et al. . |
| 5,486,537 | 1/1996 | Farinas . |
| 5,573,786 | 11/1996 | Grabo et al. . |
| 5,696,105 | 12/1997 | Hackler . |
| 5,732,719 | * 3/1998 | Godbout . |
| 5,879,326 | * 3/1999 | Godshall et al. ................ 604/51 |
| 5,947,956 | * 9/1999 | Karell . |
| 6,042,845 | * 3/2000 | Sun et al. . |

FOREIGN PATENT DOCUMENTS

1106495 * 4/1983 (SU) .
1102592 * 7/1984 (SU) .

* cited by examiner

Primary Examiner—Richard K. Seidel
Assistant Examiner—LoAn H. Thanh
(74) Attorney, Agent, or Firm—Stevens, Davis, Miller & Mosher, LLP

(57) ABSTRACT

A set depth nail notcher for cutting a notch of predetermined depth in a nail plate comprising a handle having a smooth flat surface, a longitudinal cutting edge protruding from the smooth flat surface to a height equal to the predetermined depth of the notch. A method for treating nail, especially toenail, fungus comprising cutting a notch to a predetermined depth in a nail or a toe of finger infected with fungus and applying a topical anti-fungal medication to the toe or finger through the notch.

30 Claims, 2 Drawing Sheets

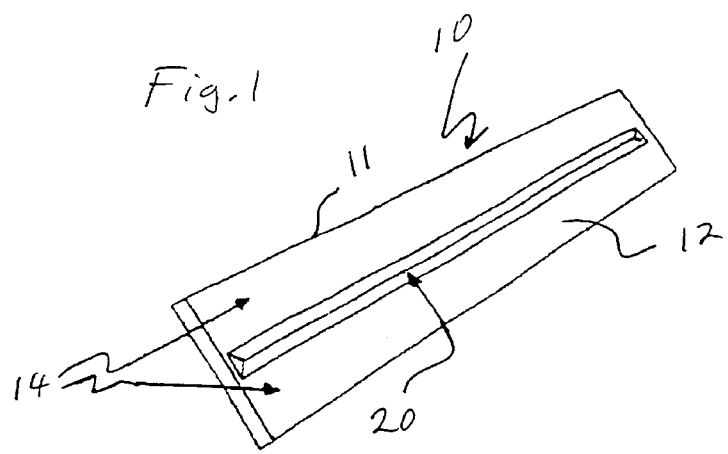
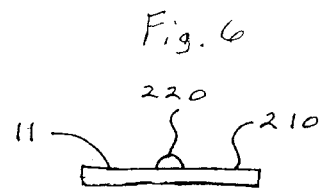
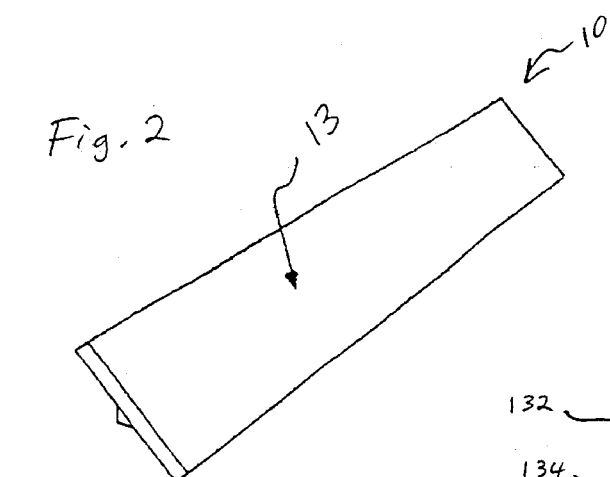
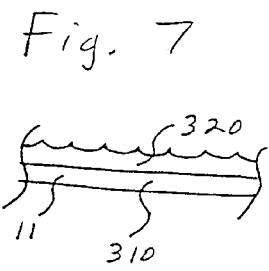
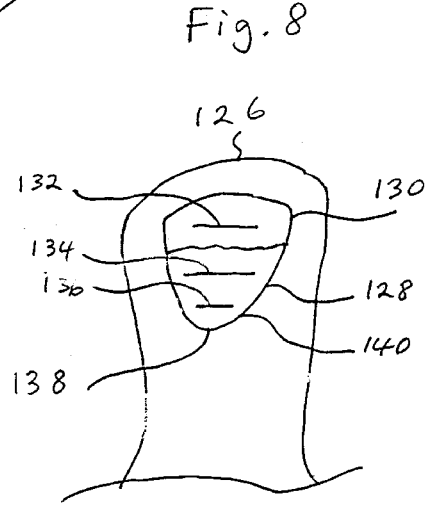

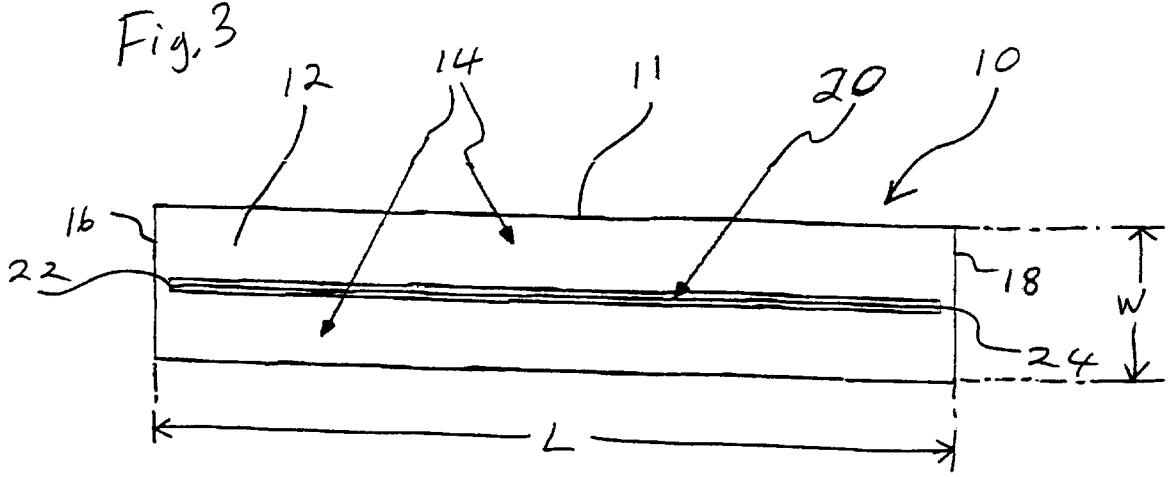
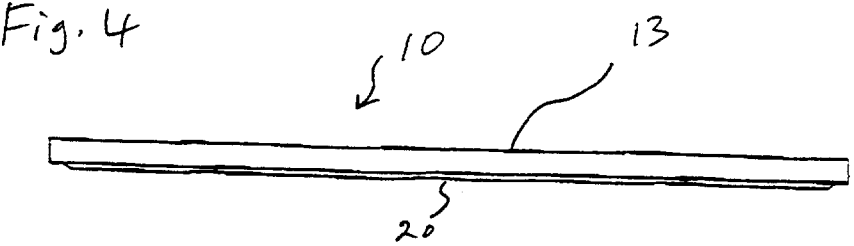
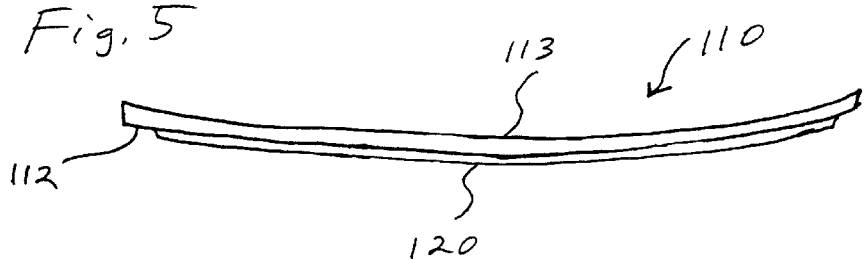

SET DEPTH NAIL NOTCHER AND METHOD FOR TREATING NAIL FUNGUS

BACKGROUND OF THE INVENTION

1. Field of the Invention

The present invention relates to a nail notcher for cutting a notch in a nail plate. The present invention also relates to a method for applying topical anti-fungal composition to fungus underneath a nail by applying the composition through the notch cut by the nail notcher of the present invention.

2. Background Discussion

A human's nail has a nail plate, which is a hard outer surface of dead cells and a nail bed below the nail plate. The nail plate is non-porous, whereas the nail bed is porous. There is soft flesh beneath the nail bed. The nail plate and the nail bed are relatively insensitive to pain. The underlying flesh is sensitive to pain. The nail plate, nail bed, and, in severe cases, the flesh below the nail bed can be infected by a wide variety of common fungi. Such fungi are responsible for nail infections, medically known as onychomycosis. Examples of onychomycosis are caused by fungi, such as *trichophyton mentagrophytes, candida albicans* or *trichophyton rubrum*. Other terms for onychomycosis are ringworm of nails or *tinea unguium*.

It is difficult to treat such infections. Although the infections are highly localized, they are located in a part of the body which is difficult to reach. U.S. Pat. No. 5,573,786 discloses application of the composition for treating fungal diseases of the skin and mucus membrane with a small, pointy wooden stick or thin plastic porous plastic stick, or brush for treating large areas. Its Example 11 discloses onychomycosis treatment of a fingernail. However, the Example emphasizes that its preparation is suitable for treating superficial onychomycotic infections. In the case of infection of the nail bed, however, therapy must be carried out together with an oral antimycotic. U.S. Pat. No. 5,573,786 is incorporated herein by reference.

U.S. Pat. No. 5,696,105 discloses drilling holes in nails to apply anti-fungal medication, as an attempt to improve topical administration of medication. U.S. Pat. No. 5,696,105 also discloses other local measures to treat nail fungus include mechanical ablation of affected nail areas, or nail removal. U.S. Pat. No. 5,696,105 is incorporated herein by reference. U.S. Pat. No. 5,696,105 also discloses application of anti-fungal medication with a brush or an applicator tipped bottle.

Rather than directly applying topical anti-fungal medication, systemic treatments are also employed. However, such systemic treatments spread medication throughout the patient's body. Thus, the medicine is not concentrated in the infected area and may cause side-effects.

It would be desirable to provide a medication for treating nail fungus, particularly toenail fungus, which easily can be directly applied to the nail to result in effective, painless and bloodless treatment.

SUMMARY OF THE INVENTION

It is an object of the invention to provide a set depth nail notcher for cutting a notch in a toenail plate.

It is another object of the invention to provide a method for applying topical anti-fungal medication to an infected nail area through a notch cut in the nail plate by the set depth nail notcher of the present invention.

In its apparatus respects, the present invention relates to a set depth nail notcher for cutting a notch of predetermined depth in a fingernail or a toenail plate. The nail notcher comprises a handle having a smooth flat surface and a longitudinal cutting edge protruding from the smooth flat surface. The longitudinal cutting edge protrudes from the smooth flat surface to a height equal to the predetermined depth of the notch. If desired, the set depth nail notcher may provide a smooth convex surface rather than a smooth flat surface for a cutting edge to protrude therefrom.

In its method respects, the present invention involves a method for treating fingernail or toenail fungus comprising employing the above-described nail notcher to cut a notch to a predetermined depth in a fingernail or a toenail infected with fungus. Then a topical anti-fungal medication is applied to the nail bed of the finger or toe through the notch cut by the above-described nail notcher. As many as two or three notches may be employed on each nail. The method treats the infected nail to create a sterile antiseptic area proximal to the cuticle of the infected nail. Then the infected area grows distally away from the cuticle and is eventually trimmed off. The sterile area typically extend into the nail bed and may extend into the underlying flesh.

BRIEF DESCRIPTION OF THE DRAWINGS

The present invention is illustrated by the below-described drawings, wherein like elements are labeled with like numerals.

FIG. 1 discloses a perspective bottom view of the first embodiment of the present invention.

FIG. 2 discloses a perspective top view of the embodiment of FIG. 1.

FIG. 3 discloses a bottom view of the embodiment of FIG. 1.

FIG. 4 discloses a side view of the embodiment of FIG. 1.

FIG. 5 discloses a side view of a second embodiment of the present invention.

FIG. 6 discloses a front view of a third embodiment of the present invention.

FIG. 7 discloses a partial side view of a fourth embodiment of the present invention.

FIG. 8 discloses an infected toenail being treated according to the present invention.

DETAILED DESCRIPTION OF THE PREFERRED EMBODIMENTS

FIG. 1 shows a first embodiment of a nail notcher 10 of the present invention. The nail notcher 10 has a handle 11 and a cutting (notching) edge 20. The handle 11 has a smooth flat bottom surface 12 and a smooth, flat top surface 13 (FIG. 2). The cutting edge 20 protrudes from the smooth, flat bottom surface 12. The cutting edge 20 may be attached to or integral with the handle 11.

As shown in FIG. 3, the handle 11 has a first end 16 and a second end 18. Likewise, the cutting edge 20 has a first end 22 and a second end 24. The first end 22 of the cutting edge 20 may be at or adjacent the first end 16 of the handle 11. The second end 24 of the cutting edge 20 may also be at or adjacent to the second end 18 of the handle 11. FIG. 3 shows first end 22 of the cutting edge 20 being adjacent the first end 16 of the handle 11. FIG. 3 also shows the second end 24 of the cutting edge 20 being adjacent the second end 18 of the handle 11. (Of course, although not shown, the cutting edge ends may extend to the handle ends.)

The cutting edge 20 may contain a straight edge, abrasive or saw-toothed (notched) edge which is capable of penetrating the nail plate to expose the nail bed. In particular, the edge may be a sharp straight edge (as shown in FIG. 3) or round (as shown in FIG. 6) or serrated (as shown in FIG. 7) to expose the maximum area of the nail plate for maximum penetration of medication. The nail notcher 10 is capable of producing an exact depth notch limited by the depth of the cutting edge 20 and the smooth shoulders 14 on either side of the cutting edge 20. For example, the cutting edge 20 may have a depth of about 1 to about 4 mm.

The nail notcher 10 is typically made of a material able to be autoclaved or sanitized. For example, the nail handle 11 may be made of metal or plastic. The cutting edge 20 is made of metal or any other material suitable for cutting. Also, combinations such as laminates of metal or plastic are possible for the handle 11. The nail notcher 10 can either be a flat nail notcher 10 (as shown in FIGS. 1–4) or be a curved nail notcher 110 (the second embodiment as shown in FIG. 5). The nail notcher 10 typically has a surface length "L" (FIG. 3) of from about 1 to about 5 inches. The nail notcher 10 also generally has a width "W" of from generally about ⅜ inch to about 1 inch. In general, the nail notcher 10 is sized for easy gripping and use. Thus, it may be provided with additional features to facilitate gripping and use, such as clamps or protrusions from the upper surface or the nail handle may have contoured side edges, etc.

FIG. 5 shows a second embodiment of the nail notcher 110 of the present invention having a smooth continuous concave surface 112 from which a cutting edge 120 protrudes. Curved nail notcher 110 also has a convex top surface 113. However, if desired, the top surface may be flat even though the opposed surface 112 is concave.

FIG. 6 shows a third embodiment of a nail notcher 210 of the present invention having a handle 11 as in the first embodiment of FIG. 1, but provided with a rounded cutting edge 220 having an abrasive surface of abrasive material conventionally employed with nail files or a rough metal surface. This embodiment is advantageous because it cuts a wider groove in the nail than would a sharp edge. This wide groove exposes more nail bed area for applying the topical medication. For example, the groove may be wider than it is deep.

FIG. 7 shows a side view of a fourth embodiment of the present invention of a nail notcher 310 having a handle 11 provided with a serrated cutting edge 320.

Any of the above nail notchers may be employed to treat nail fungus. Typically, a nail notcher, such as nail notcher 10, would be employed as follows. A patient or medical professional would rub the cutting edge of the nail notcher on a nail to abrade the nail plate to a prescribed depth. The abrading of the nail plate would occur by rubbing the surface of the nail with the nail notcher 10 until the cutting edge penetrates sufficiently deep into the nail for the smooth flat bottom surface 12 to contact the nail bed. In some instances, two or three notches may be made in the same nail for application of medication to multiple locations. In other instances, one notch may suffice. The notch (or notches) should expose the nail bed below the hard outer surface of the nail for subsequent application of topical anti-fungal medication which is then absorbed and, preferably, permeates the nail bed. The nail bed is the soft porous layer of the nail between the nail plate and the flesh below the nail.

The smooth flat bottom surface 12 prevents the cutting edge from cutting too deeply into the nail. Thus, the cutting edge 20 cuts into the nail bed and may cut to, but preferably not through, the underlying flesh. If the flesh is contacted, the contact is slight and does not cause bleeding. Thus, the present method is a bloodless procedure. Due to the porous nature of the nail bed, the notch may be sufficiently deep for applying medication for treating fungus without contacting the underlying flesh. This is particularly the case where the flesh is not infected.

Although a smooth flat bottom surface 12 is disclosed, any surface which provides depth stopping surface along at least one side of the length of the cutting edge 20 may be employed. For example, the bottom surface may comprise ribs (not shown) parallel to the cutting edge 20 to control cutting depth.

If the initially employed nail notcher does not cut a notch sufficiently deep to penetrate the hard outer surface of the nail, then a nail notcher having a cutting edge to provide a deeper cut than the already used nail notcher would be employed.

After cutting the appropriate notch or notches, a topical anti-fungal medication would be applied through the notch or notches. The medication could be any of the FDA (Food and Drug Administration) approved anti-fungal medications already in use. The topical medication would be placed into the notch (or notches) and then diffuse through the nail bed into the infected area under the nail. Typical anti-fungal medications which may be employed with the nail notcher 10 of the present invention include chlortrimizol, tolnaftate and undecylenate acid. In addition to the active ingredient, pharmaceutically acceptable adjuvants, stabilizers, preservatives, whiteners, buffers and surfactants may be used in the formulations employed with the present invention. The antifungal composition may be in the form of liquid, gel, semi-solid, cream or solid. It also may be applied as one form, e.g., liquid, which then converts, e.g., dries, to a another form, e.g., solid.

Thus, the present invention penetrates the nail plate to expose the nail bed, by an exact depth notch limited by the depth of the cutting edge and the smooth shoulders on either side of the sharp or abrasive edge to facilitate treatment.

For example, as shown in FIG. 8, notches 132, 134, 136 are cut with nail notcher 10 into a toenail 128. FIG. 8 shows fungus infecting a distal region 130, relative to the cuticle 138, of the toenail 128. Notch 132 is cut into the infected region 130. Notches 134, 136 are cut into an uninfected region 140 of the nail 128 which is proximal to the cuticle 138. In severe cases all the notches may be cut into an infected portion of nail because little or no uninfected portion is accessible. In some instances the toenail 128 may be filed to smooth its surface prior to cutting the notches into the surface.

After the notches are cut, at least one medicine which is a fungicide (kills fungus) or a fungistat (prevents fungus growth) is applied to the notches 132, 134, 136. The notches 132, 134, 136 are cut sufficiently deep to cut into the bed of the nail 128. Thus, the medication passes into the notches 132, 134, 136 and through the nail bed. This creates a sterile antiseptic area under the treated portions of the nail, especially for the proximal region 140. As noted above, the medicine may not kill fungus. However, it at least prevents its growth. Thus, the treatment prevents the fungus in the infected portion 130 from spreading to the uninfected portion 140. Then antifungal medicine is routinely reapplied to the notches for a sufficient number of days or weeks. During this treatment time, the nail continues to grow and the infected portion 130 grows distally away from the cuticle 138 and is eventually trimmed off to remove the infection from the patient.

The present invention is a major advance in treating nail, especially toenail, fungus because it provides for an easy to make, and not too deep, notch into the nail bed. This makes it easy and relatively painless for patients to treat themselves or be treated by a physician or nurse. Also, to apply the topical antifungal medication directly to the nail bed is a major advance. This will make the topical antifungal medications already on the market more effective because they will now directly, contact the nail bed and permeate into the nail bed.

It should be apparent that embodiments other than those specifically described above come within the spirit and scope of the present invention. Thus, the present invention is not limited by the above-described embodiments, but rather by the claims appended hereto.

What is claimed is:

1. A set depth nail notcher for cutting a notch of predetermined depth in a nail plant comprising:
    a handle having an upper surface and a bottom surface;
    means, comprising an elongate longitudinal notching edge, for notching the nail plate of a nail by a back and forth rubbing motion on the nail in a direction along a longitudinal axis of the notching edge, the means for notching protruding from the bottom surface to a height for notching the predetermined depth of the notch, wherein at least a portion of the bottom surface provides a surface to prevent the notching edge from notching deeper than the predetermined notch depth, wherein the notch depth is sufficient to notch through a nail bed under the nail plate.

2. The nail notcher of claim 1, wherein the bottom surface has a smooth, flat surface and the notching edge protrudes from the bottom surface to a height equal to the predetermined depth of the notch.

3. The nail notcher of claim 1, wherein the longitudinal elongate notching edge has longitudinal sides and is located on the bottom surface to define two smooth shoulders of surface, each shoulder being lateral to one longitudinal side of the notching edge.

4. The nail notcher of claim 1, wherein the notching edge has a first longitudinal end and a second longitudinal end,
    the bottom surface has a first longitudinal end and a second longitudinal end,
    the first longitudinal end of the notching edge is at a location selected from the group consisting of at the first longitudinal end of the bottom surface and adjacent the first longitudinal end of the bottom surface,
    the second longitudinal end of the notching edge is at a location selected from the group consisting of at the second longitudinal end of the bottom surface and adjacent the second longitudinal edge of the bottom surface; and
    the substrate comprises at least one member of the group consisting of metal and plastic and laminates thereof, and the substrate has a length of about 1 to about 5 inches.

5. The nail notcher of claim 1, wherein the notching edge comprises an abrasive surface.

6. The nail notcher of claim 5, wherein the notching edge abrasive surface comprises a convex abrasive surface.

7. The nail notcher of claim 1, wherein the notching edge comprises serrated metal.

8. The nail notcher of claim 1, wherein the notching edge comprises an elongate longitudinal straight edge.

9. The nail notcher of claim 1, wherein the substrate bottom surface comprises a smooth surface.

10. The nail notcher of claim 1, wherein the notcher comprises only one said elongate longitudinal edge per substrate.

11. The nail notcher of claim 1, wherein said height for cutting the predetermined depth is from 1 mm to 4 mm.

12. A method for treating fungus comprising:
    cutting an elongate continuous notch to a predetermined depth in a nail selected from the group of toenail and fingernail infected with fungus by rubbing a means for notching a nail comprising a set depth nail notcher on a nail plate of the nail, the nail notcher comprising:
    a handle having an upper surface and a bottom surface;
    an elongate notching edge protruding from the bottom surface to a height of the predetermined depth of the notch;
    applying a topical anti-fungal medication to the toenail or fingernail through the notch, wherein said predetermined depth is sufficient to penetrate the nail plate and contact a nail bed of the nail, but at most about the thickness of the nail,
wherein the notching edge is rubbed by a back and forth motion on the nail in a direction along a longitudinal axis of the notching edge.

13. The method of claim 12,
    wherein at least a portion of the bottom surface is rubbed on the nail plate, wherein the notching edge is cut through the nail plate.

14. The method of claim 13, wherein the bottom surface has a flat, smooth surface.

15. The method of claim 14, wherein the notching edge does not contact tissue under the nail bed of the nail.

16. The method of claim 13, wherein the notching edge has a first longitudinal end and second longitudinal end,
    the bottom surface has a first longitudinal end and a second longitudinal end,
    the first longitudinal end of the notching edge is at a location selected from the group consisting of at the first longitudinal end of the bottom surface and adjacent the first longitudinal end of the bottom surface,
    the second longitudinal end of the notching edge is at a location selected from a group consisting of the second longitudinal end of the bottom surface and adjacent the second longitudinal edge of the bottom surface; and
    the substrate comprises at least one member of the group consisting of metal and plastic and laminates thereof, and the substrate has a length of about 1 to about 5 inches.

17. The method of claim 12, wherein the longitudinal notching edge has a longitudinal sides and is located on the bottom surface to define two smooth shoulders of surface, each shoulder being lateral to one longitudinal side of the notching edge, further comprising rubbing at least a portion of each shoulder on the nail.

18. The method of claim 12, wherein the notching edge comprises an abrasive surface, wherein the notching edge abrades the nail during said notching.

19. The method of claim 18, wherein at least a portion of the abrasive surface is convex.

20. The method of claim 12, wherein the notching edge comprises serrated metal.

21. The method of claim 12, wherein the notching edge comprises an elongate longitudinal straight edge.

22. The method of claim 12, wherein the substrate bottom surface is a longitudinally convex surface.

23. The method of claim 12, wherein the notch is notched into a bed of the nail and the topical anti-fungal medication diffuses from the notch into the nail bed to contact flesh under the nail.

24. The method of claim 12, wherein the topical anti-fungal medication comprises at least one member selected from the group consisting of a fungicide and a fungistat.

25. The method of claim 12, further comprising the steps of trimming an infected portion of the nail away from the nail after application of the topical anti-fungal medication.

26. The method of claim 12, wherein the notch is a rounded groove.

27. The method of claim 12, wherein the notch is formed by rubbing the notching edge against the nail in a back and forth motion along a direction transverse to a longitudinal direction of the nail, forming the notch removes a portion of the nail, and the notch is formed to be transverse to the longitudinal direction of the nail.

28. The method of claim 12, wherein the height of the notching edge which protrudes from the bottom surface is constant.

29. A method for treating fungus comprising:

notching an elongate continuous notch to a predetermined depth in a nail selected from the group of a toenail and a fingernail infected with fungus by rubbing back and forth a means for notching the nail comprising a set depth nail notcher on a nail plate of the nail into a nail bed of the nail, the nail notcher comprising:

a substrate having an upper surface and a bottom surface;

an elongate notching edge protruding from the bottom surface to a height of the predetermined depth of the notch;

applying a topical anti-fungal medication to the toenail or fingernail through the notch, wherein said predetermined depth is a depth from 1 mm to 4 mm.

30. The method of claim 29, wherein the notch is formed by rubbing the notching edge against the nail back and forth along a direction transverse to a longitudinal direction of the nail, forming the notch removes a portion of the nail, and the notch is formed to be transverse to the longitudinal direction of the nail.

* * * * *